United States Patent
Kwun et al.

(10) Patent No.: US 7,913,562 B2
(45) Date of Patent: Mar. 29, 2011

(54) FLEXIBLE PLATE MAGNETOSTRICTIVE SENSOR PROBE FOR GUIDED-WAVE INSPECTION OF STRUCTURES

(75) Inventors: Hegeon Kwun, San Antonio, TX (US); Albert J. Parvin, San Antonio, TX (US); Ronald H. Peterson, Helotes, TX (US)

(73) Assignee: Southwest Research Institute, San Antonio, TX (US)

( * ) Notice: Subject to any disclaimer, the term of this patent is extended or adjusted under 35 U.S.C. 154(b) by 328 days.

(21) Appl. No.: 12/201,989

(22) Filed: Aug. 29, 2008

(65) Prior Publication Data
US 2010/0052669 A1    Mar. 4, 2010

(51) Int. Cl.
G01N 29/04    (2006.01)
G01N 29/00    (2006.01)

(52) U.S. Cl. .............................. 73/622; 73/624; 73/618

(58) Field of Classification Search .................... 73/620, 73/622, 643, 618, 627; 324/240, 262
See application file for complete search history.

(56) References Cited

U.S. PATENT DOCUMENTS

| | | |
|---|---|---|
| 3,170,114 A | 2/1965 | Placke |
| 3,568,049 A | 3/1971 | Barton |
| 4,510,447 A | 4/1985 | Moyer |
| 4,543,528 A | 9/1985 | Baraona |
| 4,784,762 A | 11/1988 | Taliaferro |
| 4,866,424 A | 9/1989 | Parks |
| 4,916,394 A | 4/1990 | Thompson |
| 5,047,719 A | 9/1991 | Johnson et al. |
| 5,314,401 A | 5/1994 | Tepper |
| 5,334,937 A | 8/1994 | Peck et al. |
| 5,456,113 A | 10/1995 | Kwun et al. |
| 5,457,994 A | 10/1995 | Kwun et al. |
| 5,479,099 A | 12/1995 | Jiles et al. |
| 5,581,037 A | 12/1996 | Kwun et al. |
| 5,841,277 A | 11/1998 | Hedengren et al. |
| 5,858,154 A * | 1/1999 | Toki .............................. 156/218 |
| 6,294,912 B1 | 9/2001 | Kwun |
| 6,373,245 B1 | 4/2002 | Kwun et al. |
| 6,373,252 B1 | 4/2002 | Eslambolchi et al. |
| 6,396,262 B2 | 5/2002 | Light et al. |
| 6,429,650 B1 | 8/2002 | Kwun et al. |
| 6,624,628 B1 | 9/2003 | Kwun et al. |
| 6,680,619 B1 | 1/2004 | Horn |
| 6,799,466 B2 | 10/2004 | Chinn |
| 6,812,707 B2 | 11/2004 | Yonezawa et al. |
| 6,917,196 B2 | 7/2005 | Kwun et al. |
| 6,967,478 B2 | 11/2005 | Waymann et al. |
| 7,053,854 B2 | 5/2006 | Plettner et al. |
| 7,183,764 B2 | 2/2007 | Goldfine et al. |
| 7,375,514 B2 | 5/2008 | Rempt et al. |
| 2004/0016299 A1 | 1/2004 | Glascock et al. |
| 2007/0100579 A1 | 5/2007 | Rempt et al. |
| 2008/0071496 A1 | 3/2008 | Glascock |

* cited by examiner

*Primary Examiner* — Lisa M Caputo
*Assistant Examiner* — Jonathan Dunlap
(74) *Attorney, Agent, or Firm* — Kammer Browning PLLC

(57) ABSTRACT

An economical, flexible, magnetostrictive sensor for use on planar and/or curved structural surfaces, for guided-wave volumetric inspection of the structure. The flexible plate MsS probe includes a flexible strip of magnetostrictive material that is adhered to the base of a flat, flexible, conductor coil assembly. The conductor coil assembly has a core that is composed of a thin flexible strip of metal, a layer of an elastomeric material, and a thin permanent magnet circuit. The flexible core is surrounded by a flat flexible cable (FFC) that is folded and looped over the layers of the core. The exposed conductors at the ends of the FFC are shifted from each other by one conductor and joined so that the parallel conductors in the FFC form a flat, flexible, continuous coil. The entire probe assembly may be bent to match the curved contours of the surface of the structure under investigation.

8 Claims, 4 Drawing Sheets

FLEXIBLE PLATE MAGNETOSTRICTIVE SENSOR PROBE FOR GUIDED-WAVE INSPECTION OF STRUCTURES

BACKGROUND OF THE INVENTION

1. Field of the Invention

The present invention relates generally to methods and systems for non-destructive testing and inspection of pipes, tubes, plates, rods, cables, and other cylindrical or plate-type structures. The present invention relates more specifically to a magnetostrictive sensor probe for use on planar and/or curved structural surfaces for guided wave inspection.

2. Description of the Related Art

Long-range, guided-wave inspection technology is an emerging technology that has the capability of quickly surveying a large volume of a structure for defects and providing comprehensive condition information on the integrity of the structure. Using relatively low-frequency (typically under 200 kHz) guided-waves in the pulse-echo testing mode, this technology performs a 100% volumetric examination of a large area of a structure and detects and locates internal and external defects in the area around a given test position. In above-ground pipelines, for example, a test range of more than 500 feet can be achieved in one direction for detecting 2% to 3% defects from a given test position. In this case, percent refers to the circumferential cross-sectional area of the defect relative to the total pipewall cross section. In plate-type structures, a test range of more than 30 feet in one direction can be achieved. In wire ropes and cables, a 300 foot longitudinal measurement in one direction can be achieved.

This guided-wave inspection technology, including the magnetostrictive sensor (MsS) technology developed at Southwest Research Institute in San Antonio, Tex., is now widely used for testing piping networks in processing plants such as refineries and chemical plants, as well as for testing plate-type structures such as containment vessels walls and the like. The technology is the only such guided-wave inspection technology that is applied to structures of many different geometries (e.g. pipe, tube, plate, rod, and cable) using a common approach with the same basic instrumentation.

For inspection of elongated structures (such as piping, tubing, rods, or cables), the Magnetostrictive Sensor (MsS) technology uses probes that are generally structured of a length of ribbon cable that encircles the structure's circumference along with a coil adapter that turns the parallel conductors in the ribbon cable into a continuous coil. For inspection of plate-type structures, plate MsS probes in the form of core type probes or flat coil type probes are used. Plate MsS probes in the form of core type probes are disclosed and described in U.S. Pat. No. 6,294,912 entitled Method and Apparatus for Non-Destructive Inspection of Plate Type Ferromagnetic Structures Using Magnetostrictive Techniques, the disclosure of which is incorporated herein in its entirety by reference. Plate magnetostrictive sensor probes in the form of flat coil type probes are disclosed and described in U.S. Pat. No. 6,396,262 entitled Method and Apparatus for Short Term Inspection or Long Term Structural Health Monitoring, the disclosure of which is incorporated herein in its entirety by reference.

For piping inspections, guided-wave probes that encircle the entire pipe circumference are presently in use. To install a guided-wave probe for piping inspection, the basic systems and methodologies require full access around the pipe circumference with about 3 to 5 inches of spacing. When access is limited to only a portion of the piping circumference, the long-range guided-wave inspection method is difficult to apply. Examples of limited access include pipelines placed very close to a wall and pipes or tubes placed closely together (such as with superheater and reheater tubes in boilers).

The encircling MsS probe used for piping inspections is generally simple and straightforward to use. However, since the probe examines the entire pipe wall cross-section all at once, it can detect and locate a defect along the length of pipe but cannot tell the defect position around the pipe circumference. If an array of relatively short (for example, equivalent to ⅛ of the pipe circumference) plate MsS probes are placed around the pipe's circumference, and the plate probes are individually controlled and operated, not only the circumferential position of a defect can be determined but also the ability to size and characterize the defect can be improved. These improvements can generally be achieved at the expense of making the MsS Probe and the associated instrument system significantly more complex, but are necessary improvements in environments where defect areas are not accessible for direct examination.

It would be desirable therefore to use plate MsS probes as may be necessarily required to investigate structures whose circumference is not entirely accessible or whose surface walls are other than planar or of a standard curvature. In other words, it would be desirable to have an economical but versatile plate MsS probe that could be utilized alone or in combination with other similar probes, to investigate structural objects having a wide variety of surfaces. To accommodate various ranges of pipe sizes and the associated curvatures, the basic plate MsS probe for the array needs to be flexible. The core-type curved plate MsS Probe (such as that disclosed in U.S. Pat. No. 6,294,912 referenced above) has limited flexibility and is relatively expensive to build. The flat coil type plate MsS Probe (such as that described in U.S. Pat. No. 6,396,262 referenced above) is more flexible. However, for relatively low frequency operations (such as 32 kHz), the required size of the flat coil type of probe (approximately 4 inch wide for 32 kHz torsional waves) becomes somewhat too large for practical use.

It would, therefore, be desirable to have not only a flexible plate type MsS probe that could be used alone or in conjunction with a number of additional probes for investigation of structures having a variety of surface curvatures, but additionally it would be desirable if such a probe was small in size, both for operational optimization and manufacturing efficiency. Once again, while such probe structures could be constructed according to some of the approaches that have been carried out before (in the referenced patent disclosures), such can generally be accomplished only through a significant increase in complexity, both for the probe and the instrumentation associated with its use. The preference would be to simplify the probe's construction and its functionality such that it would be not only simple to utilize in its application (i.e., its placement and positioning on the structure to be investigated) but also in its instrumentation and the ability of standard systems to generate guided-wave interrogation signals sufficient to identify anomalies within the structures at significant distances.

3. Background on the Magnetostrictive Effect

The magnetostrictive effect is a property peculiar to ferromagnetic materials. The magnetostrictive effect refers to the phenomena of physical, dimensional change associated with variations in magnetization. The effect is widely used to make vibrating elements for such things as sonar transducers, hydrophones, and magnetostrictive delay lines for electric signals. The magnetostrictive effect actually describes physical/magnetic interactions that can occur in two directions.

The Villari effect occurs when stress waves or mechanical waves within a ferromagnetic material cause abrupt, local dimensional changes in the material which, when they occur within an established magnetic field, can generate a magnetic flux change detectible by a receiving coil in the vicinity. The Joule effect, being the reverse of the Villari effect, occurs when a changing magnetic flux induces a mechanical vibrational motion in a ferromagnetic material through the generation of a mechanical wave or stress wave. Typically, the Joule effect is achieved by passing a current of varying magnitude through a coil placed within a static magnetic field thereby modifying the magnetic field and imparting mechanical waves into a magnetostrictive material present in that field. These mechanical or stress waves then propagate not only through the portion of the magnetostrictive material adjacent to the generating coil but also into and through any further materials in mechanical contact with the magnetostrictive material. In this way, non-ferromagnetic and/or non-magnetostrictive materials can serve as conduits for the mechanical waves or stress waves that can thereafter be measured by directing them through these magnetostrictive "wave guides" placed proximate to the magnetostrictive sensor element.

The advantages of magnetostrictive sensors over other types of vibrational sensors become quite clear when the structure of such sensors is described. All of the components typically utilized in magnetostrictive sensors are temperature, pressure, and environment-resistant in ways that many other types of sensors, such as piezoelectric based sensors, are not. High temperature, permanent magnets, magnetic coils, and ferromagnetic materials are quite easy to produce in a variety of configurations. Further, although evidence from the previous applications of magnetostrictive sensors would indicate the contrary, magnetostrictive sensors are capable of detecting mechanical waves and translating them into signals that are subject to very fine analysis and discrimination.

Examples of efforts that have been made in the past to provide systems and methods for positioning sensors in connection with the inspection of longitudinal cylindrical structures such as pipes and tubes include those disclosed in the following U.S. Patents:

U.S. Pat. No. 4,543,528 issued to Baraona on Sep. 24, 1985 entitled Flexible Probe Assembly for Use in Non-Destructive Testing of a Convex Workpiece Surface describes a complicated frame structure that includes a flexible array of sensor heads that are arranged I tension to conform to the pipe when directed against its convex surface. Multiple sensor heads are required in order to provide compliance with the curved surface of the pipe.

U.S. Pat. No. 7,183,674 issued to Goldfine et al. on Feb. 27, 2007 entitled Method for Inspecting a Channel Using a Flexible Sensor describes a system and method for the inspection of components having limited access utilizing a pressurized elastic support structure to position a number of small sensor probes. The probes themselves are not specifically identified as flexible in nature as much as being small enough to be urged against the interior surfaces of a channel using the inflatable elastic structure.

U.S. Pat. No. 7,375,514 issued to Rempt et al. on May 20, 2008 entitled Flexible Handheld MR Scanning Array for Cracks/Flaws describes an NDE device with a sensor probe constructed on a flexible membrane. A frame supports the membrane and incorporates wheels for translation across the surface being inspected. The device is primarily directed to smoothly curved surfaces as may typically be found in aircraft structures.

U.S. Pat. No. 6,967,478 issued to Wayman et al. on Nov. 22, 2005 entitled Pipe Condition Detecting Apparatus describes a fully encircling array of individual sensors for placement in contact with the external wall of a pipeline. The device includes means for inducing and detecting magnetic flux at a location on the pipeline and determining whether changes in magnetic flux reflect changes in the condition of the pipe wall.

U.S. Pat. No. 5,334,937 issued to Peck et al. on Aug. 2, 1994 entitled Magnetic Field Gradient Coil and Assembly describes a magnetic field gradient coil for use in imaging techniques over and within a cylindrical structure. The coil is established through the use of an array of parallel conductors oriented in varying directions around and along the length of the cylindrical structure.

U.S. Pat. No. 6,680,619 issued to Horn on Jan. 20, 2004 entitled Sensoring Device for Monitoring Potential on Corrosion Threatened Objects describes an array of individual sensors positioned on an encircling band about a cylindrical structure such as a pipe. A number of individual cables are connected to the plurality of sensors arranged in a matrix defining measurement points with specifically identified distances.

U.S. Pat. No. 4,784,762 issued to Taliaferro entitled Magnetic Trap describes a method for positioning a Hall Effect sensor on the external surface of a cylindrical pipe. The structure includes a magnetic trap positioned in conjunction with a magnetically transparent sheet on one side of which a magnet is mounted to produce a magnetic field. The Hall Effect sensor is positioned adjacent the magnet to sense the magnetic field.

U.S. Pat. No. 3,568,049 issued to Barton on Mar. 2, 1971 entitled Adjustable Search Shoe for Use in Non-Destructing Testing of Tubular Members describes a sensor structure that includes an object engaging surface that may be mechanically adjusted to change its curvature so as to conform to the wall of the pipe or tubular object under inspection.

U.S. Pat. No. 5,479,099 issued to Jiles et al. on Dec. 26, 1995 entitled Magnetic Inspection Heads Suited for Contoured or Irregular Surfaces describes an arrangement of coils associated with an array of moveable pins within an assembly that is positioned against the curved surface of a pipe or tube. The pins adjust their position according to contact with the external circumference of the pipe and thereby establish a conformed contact surface for the sensor on the magnetic inspection head.

In general, the prior efforts in the field associated with cylindrical structures have been directed to partial circumference sensor structures only where the type of interrogating signal is easily suited to such configurations. That is, none of the previous efforts at partial circumferential orientation have provided suitable sensor adherence structures for use in conjunction with long-range guided-waves. These interrogating waves have heretofore been limited to propagation from sensor structures that circumferentially surround the pipe or tube. In a similar manner, the prior efforts in the field utilizing plate type MsS probes have been limited to individual use on planar structures or within arrays utilizing complex probes and support frame mechanisms, as well as complex multi-sensor operation. None of the previous efforts at either partial circumference sensor structures, or arrays of plate MsS probes, have accomplished the efficient use of such probes at a lower cost and with greater versatility.

It would therefore be desirable to have a sensor structure that was economical to manufacture and versatile in its use. The simplicity and ruggedness of its construction would contribute to the requirement for variability in the number of such sensors that might be used in a single structural investigation, while a compact size and flexibility would contribute to the versatility of use in conjunction with a wide range of curved or planar surfaces.

In the present invention, systems and methods for constructing and using such a plate MsS probe for guided-wave inspection of a variety of structures are described. The systems and methods are built upon existing magnetostrictive sensor (MsS) methods and devices, particularly the thin magnetostrictive strip approach (described in U.S. Pat. No. 6,396,262, entitled Method and Apparatus for Short Term Inspection or Long Term Structural Health Monitoring; U.S. Pat. No. 6,429,650, entitled Method and Apparatus Generating and Detecting Torsional Wave Inspection of Pipes and Tubes; and U.S. Pat. No. 6,917,196, also entitled Method and Apparatus Generating and Detecting Torsional Wave Inspection of Pipes and Tubes, the disclosures of which are each incorporated herein in their entirety by reference), and the plate MsS probe (described in U.S. Pat. No. 6,294,912, entitled Method and Apparatus for Nondestructive Inspection of Plate Type Ferromagnetic Structures using Magnetostrictive Techniques, the disclosure of which is incorporated herein in its entirety by reference), but modified and made less expensive and more versatile to fit the purposes of the present invention.

SUMMARY OF THE INVENTION

The present invention therefore describes an economical, flexible, magnetostrictive sensor (MsS) probe for use on planar and/or curved structural surfaces, for guided-wave, volumetric inspection of the structure. The flexible plate MsS probe includes a flexible strip of magnetostrictive material that is adhered to the base of a generally flat, flexible, conductor coil assembly, preferably with an elastomeric adhesive (such as silicon) or with double sided tape. The conductor coil assembly has a core that is composed of a thin flexible layer of metal, a layer of an elastomeric material (such as rubber), and a thin permanent magnet circuit. The flexible core is surrounded (top, bottom, and on the longitudinal ends) by a flat flexible cable (FFC) that is folded and looped over the layers of the core. The exposed conductors at the ends of the FFC are shifted from each other by one conductor spacing and joined together so that the parallel conductors in the FFC form a flat, flexible, continuous coil. The entire probe assembly may be bent to match the curved contours of the surface of the structure under investigation. Further features of both the system of the present invention and its method of use will become apparent from the following detailed description with reference to the appended drawing figures.

BRIEF DESCRIPTION OF THE DRAWINGS

The accompanying figures will give a fuller description and a better understanding of the details and advantages of the present invention. The drawing figures appended may be briefly described as follows.

DETAILED DESCRIPTION OF THE PREFERRED EMBODIMENTS

Figure 1:
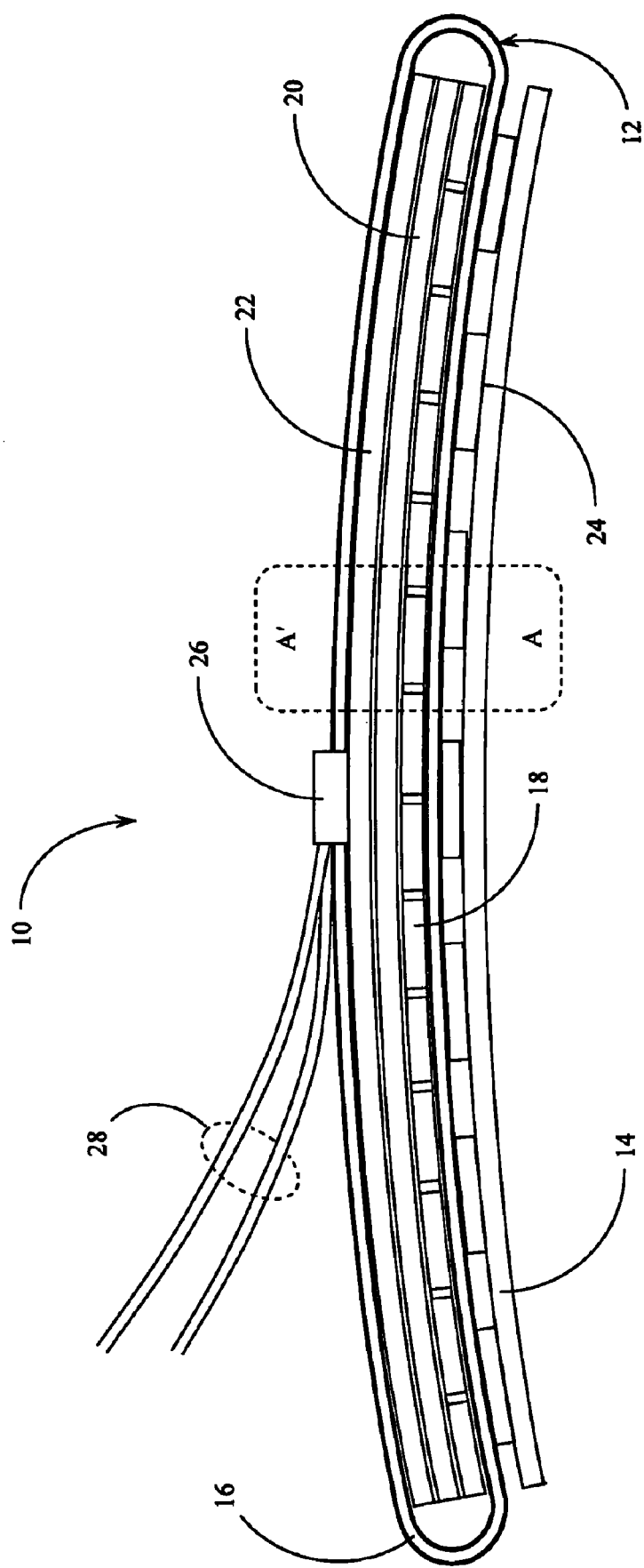
FIG. 1 is a schematic side view of the magnetostrictive sensor probe assembly of the present invention.
Figure 2:
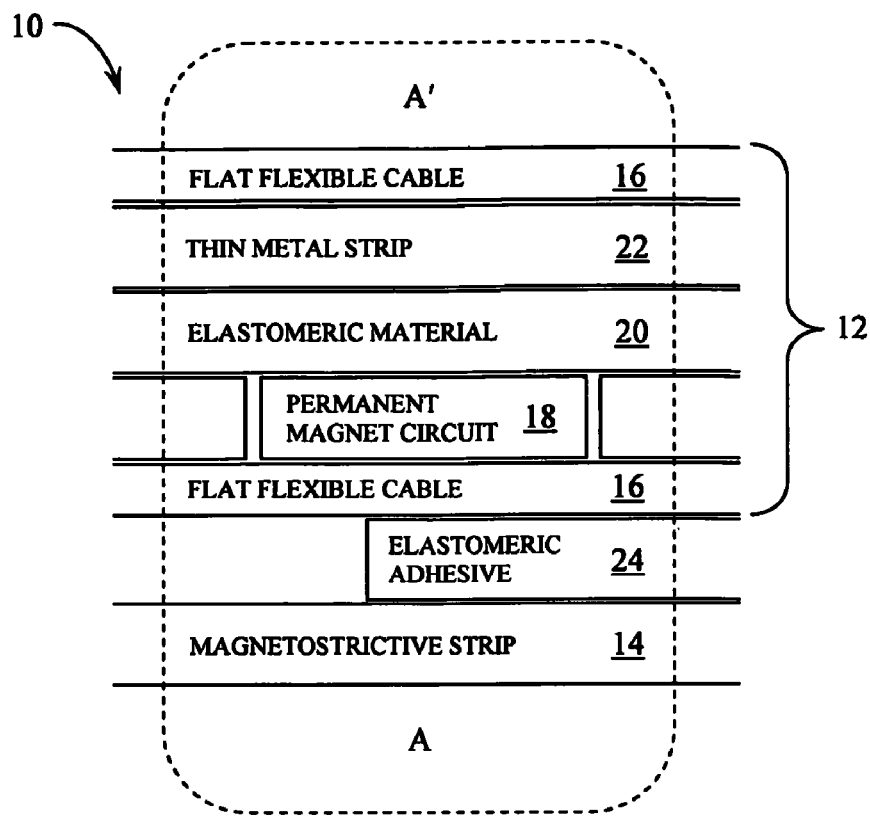
FIG. 2 is a schematic block diagram disclosing the functional layers of the magnetostrictive sensor probe assembly of the present invention as shown in the layered cross-section A-A'.
Figure 3:
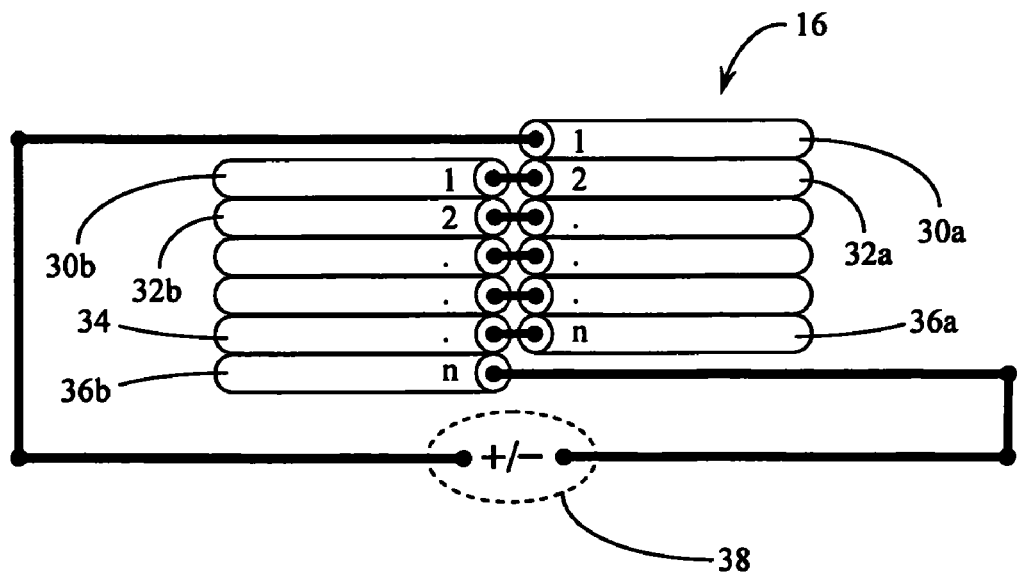
FIG. 3 is a schematic representation of the structure of the flat flexible cable (FFC) coil conductor connection of the present invention.
Figure 4A:
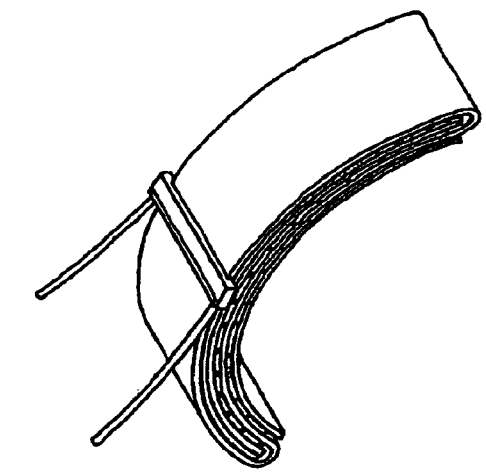
FIGS. 4A and 4B are side and perspective views the magnetostrictive sensor probe assembly of the present invention in a generally planar configuration, illustrating its flexibility.
Figure 5A:
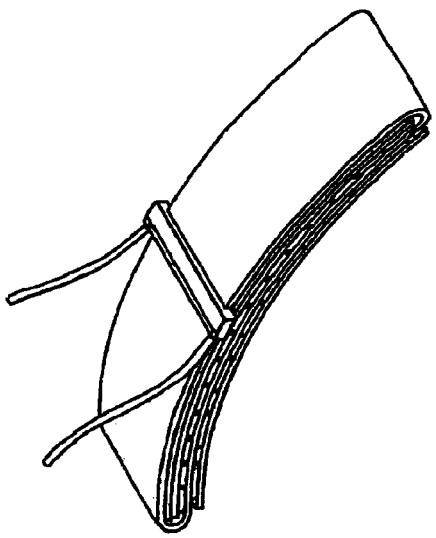
FIGS. 5A and 5B are side and perspective views the magnetostrictive sensor probe assembly of the present invention in a slightly curved configuration, illustrating its flexibility.
Figure 6A:
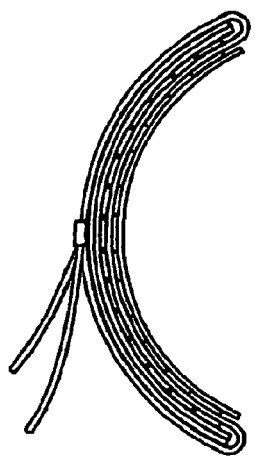
FIGS. 6A and 6B are side and perspective views the magnetostrictive sensor probe assembly of the present invention in a significantly curved configuration, illustrating its flexibility.
Figure 4B:
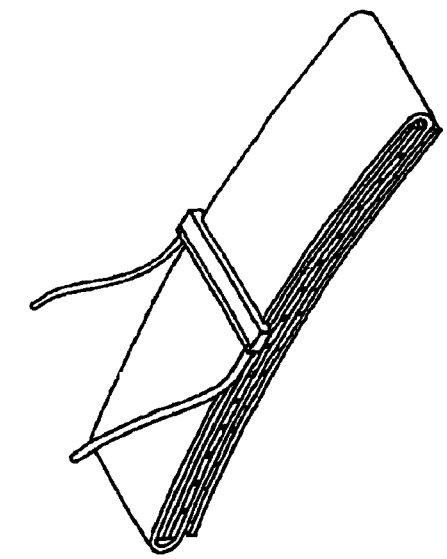
Figure 5B:
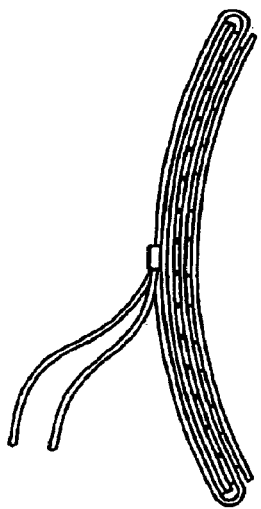
Figure 6B:
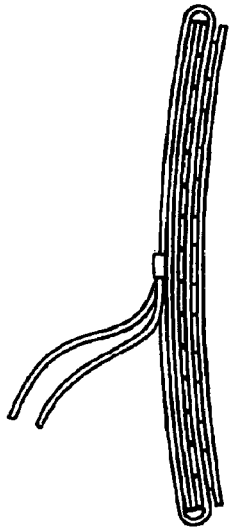

Reference is made first to FIG. 1 for a brief description of the basic structure and function of the magnetostrictive sensor probe of the present invention. FIG. 1 schematically illustrates the flexible plate MsS probe of the present invention. The probe's layered structure may best be described according to its cross-sectional configuration which, as shown functionally in FIG. 2, is composed of thin layers of: a magnetostrictive strip; a flat flexible cable (FFC); a permanent magnetic circuit comprising an array of small permanent magnets and mild steel pieces set in an elastomeric material (such as silicon); an elastomeric material (such as rubber); and a metal strip. The magnetostrictive strip is attached to the FFC using an elastomeric adhesive (such as silicon) or a double sided tape. The FFC is folded and looped over the rest of the layers. The exposed conductors at the ends of the FFC are shifted from each other by one conductor spacing and joined together so that the parallel conductors in the FFC would form a continuous coil as illustrated in FIG. 3, and described in more detail below.

FIG. 1 is a schematic side view of the flexible plate MsS probe of the present invention. In this view, the probe assembly 10 is seen to be constructed of conductor coil assembly 12 and magnetostrictive strip 14. Coil assembly 12 is constructed of flat flexible cable 16 which partially surrounds three parallel layers comprising permanent magnet circuit 18, elastomeric material 20, and metal strip 22. Magnetostrictive strip 14 is attached to conductor coil assembly 12 with a layer of adhesive such as with elastomeric adhesive 24.

The permanent magnet circuit 18 in probe assembly 10 provides a DC bias magnetic field that optimizes MsS guided-wave generation and detection. When a magnetically conditioned magnetostrictive strip 14 is used in the assembly, the permanent magnet circuit 18 may not be necessary to the operation of the sensor probe. The elastomeric material layer 20 helps to evenly distribute the pressing force (exerted from above by a clamping means described in more detail below) over the entire contacting surface of the magnetostrictive strip 14 and thus to improve uniform mechanical coupling between the magnetostrictive strip 14 and the contacting surface of the structure under investigation. The thin flexible metal layer 22 is provided to shield the time varying magnetic field produced by the upper part of the coils 16.

FIG. 2 discloses in greater detail the manner in which the various layers of the probe assembly 10 function to achieve the generation of guided-waves into the structure being investigated and to receive reflected guided-waves back from the structure to be detected within the NDE instrumentation. FIG. 2 provides a representative cross-section of the layered structure of the flexible probe assembly 10 of the present invention. In this view, taken along a cross-sectional area A-A' shown in FIG. 1, magnetostrictive strip 14 is shown as it would be placed in position against the surface of the structure being investigated. Conductor coil assembly 12, comprising the multiple layers described in more detail below, is positioned over magnetostrictive strip 14 and adhered thereto by way of elastomeric adhesive 24. Some intermittent spacing with regard to the placement of elastomeric adhesive 24 may facilitate the lateral movement of conductor coil assembly 12 with respect to magnetostrictive strip 14, as may be necessitated through the bending of the probe.

Conductor coil assembly 12 is itself comprised of internal layers surrounded by flat flexible cable 16 as described above. In this cross-sectional view it is the lower side layer of flat flexible cable 16 that provides the contact surface with magnetostrictive strip 14 through elastomeric adhesive 24. Within flat flexible cable 16 are the layers comprising thin flexible metal strip 22, elastomeric material 20, and optionally, permanent magnet circuit 18. Once again, each of these layers is constructed to allow some lateral movement of the layers upon bending of the flexible sensor probe so as to prevent buckling or separation of the layers during use.

FIG. 3 discloses in greater detail the manner in which the flat flexible cable (FFC) is arranged to create a continuous loop coil. Flat flexible cable, sometimes referred to as "ribbon cable," is commonly used with electronic circuits, often to connect one circuit board to another where a flexible path is required. Such cable is therefore relatively inexpensive although its use is almost universally limited to parallel path conductor connection. In the present invention, the FFC is used to easily establish a continuous conductor coil (that remains flexible and flat) by connecting the ends of the flat cable together after shifting the conductors by one conductor path. In this manner, as shown in FIG. 3, the first conductor 30a of one end of the cable 16 is left free for external connection while the second conductor 32a of the first end is connected to the first conductor 30b of the second end of the cable. In this manner, the $n^{th}$ conductor 36a of the first end of the cable 16 is connected to the n-1 conductor 34 of the second end of the cable 16, leaving the nth conductor 36b of the second end free for external connection. When the free conductors (one from each end of the flat cable) are connected to a current source 38, the device functions as a continuous conductor coil suitable for establishing a current varying dependent magnetic field within the volume inside and around the coil. It is this magnetic field fluctuation that initiates the magnetostrictive effect in the magnetostrictive strip of the sensor probe assembly of the present invention. The reverse magnetostrictive effect allows the sensor probe to detect the guided waves within the object structure under investigation as they move through the magnetostrictive strip and measurably alter the magnetic field within and about the coil.

Each constituent layers in the probe is flexible and can move from each other. The probe therefore can accommodate a large range of surface curvatures as illustrated in FIGS. 4A & 4B, FIGS. 5A & 5B, and FIGS. 6A & 6B.

When in use, the probe is pressed down against the surface of a structure under testing with an appropriate clamping device. The coil formed by the FFC is connected to an MsS Instrument and is activated, generating the guided-waves in the magnetostrictive strip. The generated guided-waves are then mechanically coupled to the structure and propagate along the structure. Guided-wave signals reflected back from anomalies in the structure are detected by the probe in the reverse process. Because the coil in the probe of the present invention is built vertically from the magnetostrictive strip, the required probe width is approximately ½ of the width of the flat coil-type plate probe described in the references mentioned above (for example, approximately 2 inches instead of 4 inches for 32-kHz torsional wave operation).

Figure 7:
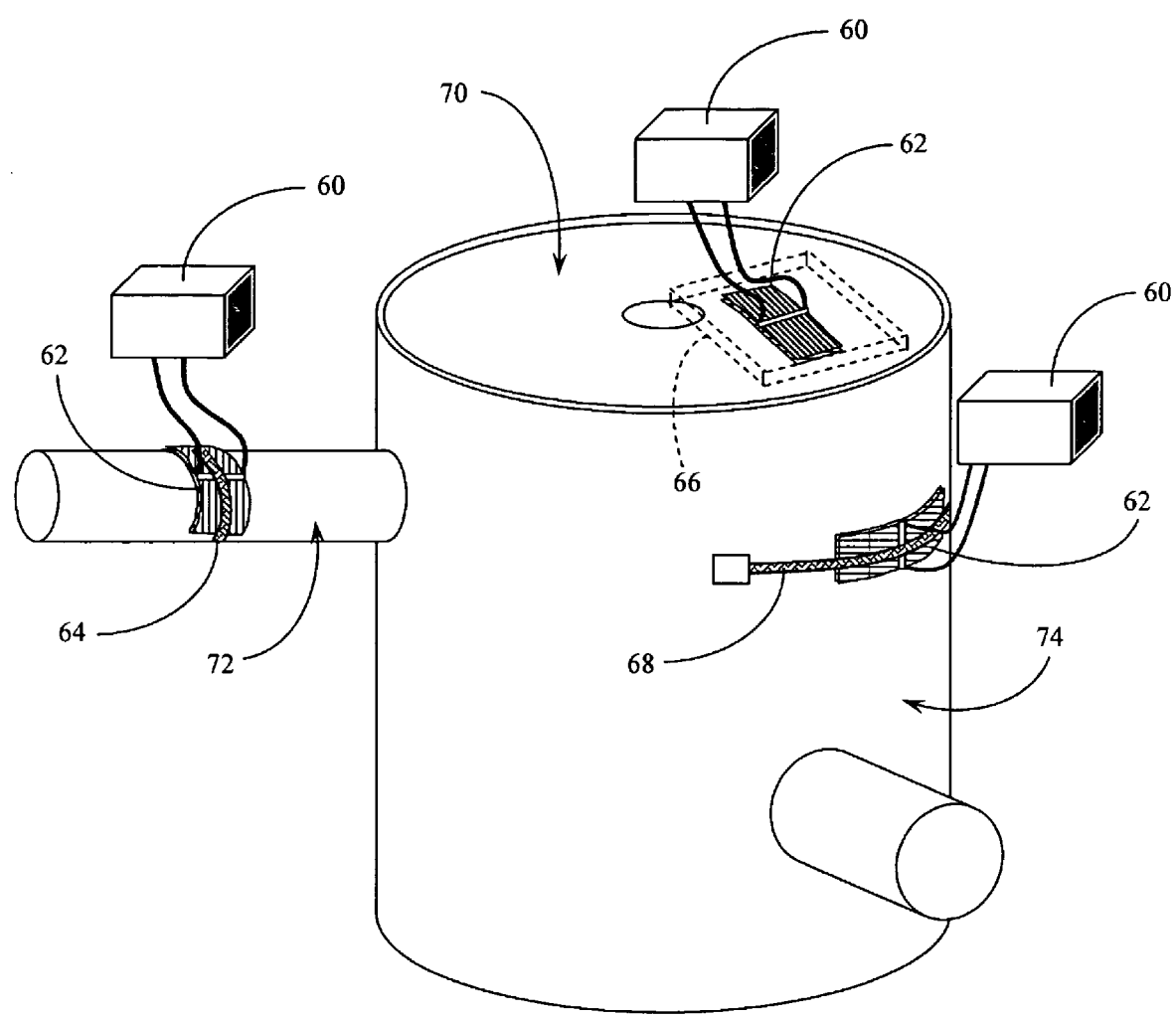
FIG. 7 is a perspective view of the manner in which the magnetostrictive sensor probe assembly of the present invention may be positioned on surfaces with a variety of curvatures and planes.

Reference is finally made to FIG. 7 for a brief description of the manner in which the MsS probe of the present invention may be utilized in conjunction with a variety of structural surfaces, varying from planar to cylindrical in curvature. FIG. 7 shows as an example of a structure to be investigated, a containment vessel with a number of inlet and outlet conduits. As shown, the same plate MsS probe 62 of the present invention may be utilized in conjunction with any of a number of different surfaces on this structure. In each instance, magnetostrictive signal instrumentation 60 is associated with the plate MsS probe 62. In a first instance, the generally planar top 70 of the containment vessel may receive probe 62 in a flat or nearly flat condition. In this instance, probe 62 may be "adhered" to the surface of the containment vessel by means of a simple weighted object 66. Because of the horizontal orientation of top 70 sufficient contact between probe 62 and the top surface 70 may be maintained through the simple pressure exerted by a modestly weighted object (for example, a flexible weighted soft cover filled with inert material sufficient to provide the necessary weight.

Alternately, probe 62 might he placed against the cylindrical side 74 of the containment vessel in a manner that results in a slight curvature to the flexible probe. In this case, securing means 68 may be required to maintain adherence of probe 62 against side wall 74 sufficient to carry out the guided-wave interrogation of the structure. Securing means 68 may be a flexible length of material that is directed across probe 62 and is removably attached to the containment vessel at its ends. This attachment might be accomplished by means of discrete magnets (if the containment vessel wall is itself ferromagnetic) or by some other means of temporary adhesion on the ends of the strap. In any event, the removable securing means should be such that the probe 62 is urged against the side wall 74 with sufficient pressure to maintain physical contact throughout the base surface of the probe. Finally, use of probe 62 on smaller cylindrical structures, such as inlet conduit 72 shown in FIG. 7, might be accomplished by means of strap 64 that may fully encircle the circumference of the smaller conduit 72. In each example shown in FIG. 7, only modest pressure is applied in order to maintain physical compliance between MsS probe 62 and the surface under investigation.

Although the present invention has been described in terms of the foregoing preferred embodiments, this description has been provided by way of explanation only and is not intended to be construed as a limitation of the invention. Those skilled in the art will recognize modifications of the present invention and its methods of use that might accommodate specific pipes, tubes, plates, rods, cables, and other cylindrical or plate-type structures, and even specific magnetostrictive sensor configurations. Such modifications as to the structures under inspection or their specific curvatures or to the sensor structures, where such modifications are merely incidental to the specific NDE environment, do not necessarily depart from the spirit and scope of the underlying invention.

We claim:

1. A flexible plate-type magnetostrictive sensor (MsS) probe for inspection of structures having surfaces that may vary from planar to cylindrical in curvature, the MsS probe comprising:
   (a) a flat flexible cable (FFC) coil assembly, the FFC coil assembly having a top face and a bottom face, the FFC coil assembly comprising:
      (i) a length of flat flexible cable (FFC) having a plurality of parallel conductors, the FFC folded back on itself and connected one end to the other after shifting the plurality of parallel conductors by one, thereby creating a continuous conductor loop coil having first and second electrical connections;

(ii) a flexible strip of metal having a top face and a bottom face; and (iii) a layer of elastomeric material positioned on the bottom face of the flexible metal strip;

wherein the metal strip is positioned within the coil constructed by folding the FFC back on itself; and (b) a flexible strip of magnetostrictive material, the flexible magnetostrictive strip adhered to the bottom face of the FFC coil assembly;

wherein time varying current in the FFC coil assembly causes guided-waves to be generated in the magnetostrictive strip, which guided-waves, when the magnetostrictive strip is positioned against the surfaces of the structure, travel to and are reflected by anomalies in the structure under inspection.

2. The MsS probe of claim 1 wherein the flexible strip of magnetostrictive material is adhered to the bottom face of the FFC coil assembly with an elastomeric adhesive.

3. The MsS probe of claim 1 wherein the flexible strip of magnetostrictive material is adhered to the bottom face of the FFC coil assembly with double sided adhesive tape.

4. The MsS probe of claim 1 wherein the FFC coil assembly further comprises:

an FFC connector block for receiving and electrically connecting the shifted plurality of parallel conductors of one end of the FFC to the other, the connector block further incorporating the first and second electrical connections to the FFC coil assembly.

5. The MsS probe of claim 1 further comprising a longitudinal strap positioned across the top face of the FFC coil assembly for urging the probe against the surface of the structure under investigation.

6. The MsS probe of claim 1 wherein the FFC coil assembly further comprises:

a thin permanent magnet circuit positioned on the layer of elastomeric material opposite from the flexible strip of metal, the permanent magnet circuit comprising an array of commonly oriented permanent magnets to establish a bias magnetic field in the magnetostrictive strip.

7. A method for making a flexible plate-type magnetostrictive sensor (MsS) probe for inspection of structures having surfaces that may vary from planar to cylindrical in curvature, the method comprising:

(a) providing a strip of flexible metal having a top face and a bottom face;

(b) positioning a layer of elastomeric material adjacent the bottom face of the metal strip;

(c) providing a length of flat flexible cable (FFC) having a top face, a bottom face, and two ends, the FFC comprising a plurality of parallel electrical conductors;

(d) positioning the metal strip and the layer of elastomeric material on the top face of the FFC;

(e) folding the ends of the FFC back on itself over the top face of the metal strip;

(f) connecting one end of the FFC to the other end of the FFC, after shifting the plurality of parallel conductors by one, thereby creating a continuous conductor loop coil having first and second electrical connections; and (g) positioning and adhering a flexible strip of magnetostrictive material to the bottom face of the FFC.

8. The method of claim 7 further comprising the steps of:

positioning a thin permanent magnet circuit positioned on the layer of elastomeric material opposite from the flexible strip of metal, the permanent magnet circuit comprising an array of commonly oriented permanent magnets to establish a bias magnetic field in the magnetostrictive strip.

* * * * *